(12) United States Patent
Doron et al.

(10) Patent No.: US 11,135,127 B2
(45) Date of Patent: Oct. 5, 2021

(54) METHOD AND DEVICE FOR PNEUMOMASSAGE

(71) Applicant: MEGO AFEK AC LTD., Kibbutz Afek (IL)

(72) Inventors: Shay Doron, Maalot (IL); Gilad Kent, Kibbutz Ramat-David (IL)

(73) Assignee: MEGO AFEK AC LTD., Kibbutz Afek (IL)

( * ) Notice: Subject to any disclaimer, the term of this patent is extended or adjusted under 35 U.S.C. 154(b) by 514 days.

(21) Appl. No.: 15/034,187

(22) PCT Filed: Nov. 6, 2014

(86) PCT No.: PCT/IL2014/050968
§ 371 (c)(1),
(2) Date: May 4, 2016

(87) PCT Pub. No.: WO2015/068163
PCT Pub. Date: May 14, 2015

(65) Prior Publication Data
US 2016/0262971 A1    Sep. 15, 2016

Related U.S. Application Data

(60) Provisional application No. 62/030,632, filed on Jul. 30, 2014, provisional application No. 61/901,018, filed on Nov. 7, 2013.

(51) Int. Cl.
*A61H 9/00* (2006.01)
*A61B 5/107* (2006.01)
*A61B 5/00* (2006.01)

(52) U.S. Cl.
CPC ......... *A61H 9/0078* (2013.01); *A61B 5/1073* (2013.01); *A61B 5/4836* (2013.01);
(Continued)

(58) Field of Classification Search
CPC ... A61H 9/0078; A61H 9/0085; A61H 9/0092
See application file for complete search history.

(56) References Cited

U.S. PATENT DOCUMENTS 4,013,069 A    3/1977  Hasty
5,279,283 A *  1/1994  Dillon .................. A61H 9/0078
                                                128/DIG. 20
(Continued)

FOREIGN PATENT DOCUMENTS

FR         2682279       4/1993
WO      2014/031409      2/2014

OTHER PUBLICATIONS

Bliss and Simini (1999) When are the seeds of postoperative pressure sores sown?. Often during surgery. BMJ 319(7214): 863-4.
(Continued)

*Primary Examiner* — LaToya M Louis
(74) *Attorney, Agent, or Firm* — The Roy Gross Law Firm, LLC; Roy Gross

(57) ABSTRACT

A device for compression therapy of a subject's body part including a compression sleeve configured to be surroundingly engageable with the body part, the sleeve having at least one bladder configured to be inflated and deflated such that an enhanced circulation is achieved and a controller configured to calculate a change in the volume of the body part by determining a change in a time required for inflating the at least one bladder from a predetermined vacuum level to a predetermined pressure level obtained during at least two inflation cycles; and to control operation of the compression sleeve based at least on the calculated change in the volume of the body part.

15 Claims, 2 Drawing Sheets

(52) U.S. Cl.
CPC ... *A61H 9/0092* (2013.01); *A61H 2201/0176* (2013.01); *A61H 2201/0184* (2013.01); *A61H 2201/50* (2013.01); *A61H 2201/5071* (2013.01); *A61H 2201/5097* (2013.01); *A61H 2205/06* (2013.01); *A61H 2205/10* (2013.01); *A61H 2209/00* (2013.01)

(56) References Cited

U.S. PATENT DOCUMENTS

| | | | |
|---|---|---|---|
| 5,830,164 | A | 11/1998 | Cone et al. |
| 5,968,073 | A | 10/1999 | Jacobs |
| 7,637,879 | B2 | 12/2009 | Barak |
| 8,313,450 | B2 | 11/2012 | Ben-Nun |
| 9,737,238 | B2 * | 8/2017 | Wright ............... A61B 5/1073 |
| 2006/0036203 | A1 | 2/2006 | Ouchene |
| 2007/0088239 | A1 | 4/2007 | Roth |
| 2008/0103397 | A1 | 5/2008 | Barak |
| 2008/0281240 | A1 | 11/2008 | Wright |
| 2010/0100017 | A1 | 4/2010 | Maguina |
| 2011/0098616 | A1 | 4/2011 | Ben-Nun |

OTHER PUBLICATIONS

Shoemake and Stoessel (2011) Pressure ulcers in the surgical patient. Kimberly-Clark Knowledge Network, The Clinical Issue 1: 1-11.

Tschannen et al., (2012) Patient-specific and surgical characteristics in the development of pressure ulcers. Am J Crit Care 21(2): 116-25.

* cited by examiner

METHOD AND DEVICE FOR PNEUMOMASSAGE

RELATED APPLICATION DATA

This application is the U.S. National Stage of International Application No. PCT/IL2014/050968 filed Nov. 6, 2014, which claims the benefit of U.S. Provisional Patent Application Nos. 61/901,018 filed Nov. 7, 2013 and 62/030,632 filed Jul. 30, 2014. Each of the foregoing applications is hereby incorporated by reference in its entirety for all purposes.

TECHNICAL FIELD

The present disclosure relates to methods and devices for providing pneumomassage to a subject in need thereof.

BACKGROUND

It is well known to treat medical conditions such as edema with pressure devices that squeeze the limb or other body part, typically by means of inflatable pressure sleeves wrapped around the limb. The pressure device moves excess fluid from engorged tissues from distal portions of the limb to proximal portions, eventually to the trunk of the body where the fluids are absorbed in the circulatory system and excreted from the body. These pressure devices thus perform external, non-invasive compression therapy and are known as intermittent pneumatic compression devices (IPC).

Deep vein thrombosis, or deep venous thrombosis, (DVT) is the formation of a blood clot (thrombus) in a deep vein, predominantly in the legs. Common symptoms of DVT include swelling of the treated body part. A DVT can cause localized tissue damage leading to permanent disability. A DVT may become life-threatening if a piece of the blood clot breaks off, travels downstream through the heart into the pulmonary circulation system, and becomes lodged in the lung thereby causing pulmonary embolism.

Lymphedema, is a condition of localized fluid retention and tissue swelling caused by a compromised lymphatic system. Symptoms may include a feeling of heaviness or fullness, edema, and aching pain in the affected area. In advanced lymphedema, there may be the presence of skin changes such as discoloration, verrucous (wart-like) hyperplasia, hyperkeratosis, and papillomatosis; and eventually deformity (elephantiasis). Lymphedema may be inherited (primary) or caused by injury to the lymphatic vessels (secondary) or due to venous insufficiency.

SUMMARY

The present disclosure relates to methods and devices for providing compression therapy to a subject in need thereof. Specifically, the disclosure relates to methods and devices for providing pneumomassage to a subject's body area by applying a compression sleeve around the area to be treated. The sleeve includes a bladder configured to be repeatedly inflated and deflated such that an enhanced circulation is achieved. The device and method enable estimating a change in the volume of the treated area by determining the time required for inflating the bladder from a predetermined vacuum level to a predetermined pressure level obtained during at least two inflation cycles; thereby enabling measuring the pre and post treatment volumes of the treated areas, and in some embodiments, controlling the operation of the compression sleeve based at least on the estimated volume change in the treated area.

It is understood by the skilled in the art that the present disclosure provides numerous advantages. Inter alia, the device and methods of the present disclosure enables providing pneumomassage to a subject in need thereof while providing information as to the treatment's effectiveness, and detect possible contraindications that could appear during the course of the therapy. For example, the device and methods of the present disclosure may be particularly suitable for use in pneumatic compression therapy as prophylaxis for deep vein thrombosis (DVT), as pneumatic compression therapy are highly effective for prophylaxis of DVT, but may be contraindicated if a DVT forms during treatment. Since patients are prescribed DVT prophylaxis because they are at heightened risk for developing DVT, the development of a DVT during prophylaxis is a distinct possibility, and the ability to detect a DVT that forms during IPC therapy will provide a considerable advantage to IPC systems used as prophylaxis for this condition. As another example, the device and methods of the present disclosure may be suitable for use in the treatment of lymphedema.

According to some embodiment, the IPC treatment parameters may be altered as a result of treatment response. Optional IPC parameters include, but are not limited to pressure, time, frequency, massage mode or any combination thereof. Each possibility is a separate For example, an increase in the circumference and/or volume of the treated body part, especially in patients who have lymphedema due to obstruction of the lymphatics, may indicate that the prescribed treatment regimen should be altered.

Non-limiting examples of altering the IPC parameters include increasing or decreasing pressure, changing the appliance, changing the massage mode, applying adjunctive therapies, discontinuing treatment or any combination thereof. Each possibility is a separate embodiment.

Furthermore, the IPC device disclosed herein may advantageously inform the user and/or operator of the device about a swelling detected in the treated body part. Since treatment is often self-administered by the patient at home, a device capable of informing the user and/or operator of a detected swelling may provide a considerable advantage.

Methods for determining the girth of a body part during compression therapy are known in the art. However, there remains a need for a device and method for determination of the volume of the body part which is reliable and consistent enough to enable intra and inter patient comparison. Generating a vacuum in the bladder prior to inflation advantageously enables to reliably determine the time required to subsequently reach a predetermined pressure level in the bladder, disregarding patient differences such as for example the weight of the patient or the normal volume of patient's treated body part. For accurate results the inflation time should be measured from the same bladder start position. Since the bladders usually have remnant air inside, the only way to achieve the same starting point is to deflate the bladder to the vacuum level.

Changes in the volume of the body part may serve as an indication of the treatment efficacy. Ideally volume will be maintained or reduced. An increase in pretreatment volume may indicate noncompliance. An increase in treatment volume during or after treatment may indicate the need to adjust the patient's treatment regimen, such as increasing or decreasing pressure, adding adjunctive therapies or adjusting the fit of the compression wrap, as well as indicate a need to evaluate the patient for development of a contraindication, such as DVT, as indicated above. The technology, disclosed herein, will be a great advance over current practice, which typically uses a tape measure to take circumferential measurements at various points along the treated area to calculate volume of the treated body part. The method, disclosed herein, enabling the assessment of volume changes during and after treatment provides a potentially powerful tool in monitoring, documenting, and demonstrating efficacy of the prescribed therapy, particularly in cases when patient self-administers the IPC treatment at home, far from the eye of a trained physical therapist or physician.

The following embodiments and aspects thereof are described and illustrated in conjunction with systems, tools and methods which are meant to be exemplary and illustrative, not limiting in scope. Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

There is provided, according to some embodiments, a device for compression therapy of a subject's body part, the device comprising: a compression sleeve configured to be surroundingly engageable with the body part, the sleeve comprising at least one bladder configured to be inflated and deflated such that enhanced circulation is achieved; a controller configured to calculate and/or estimate a change in the volume of the subject's body area by determining a change in the time required for inflating at least one bladder from a predetermined vacuum level to a predetermined pressure level obtained during at least two inflation cycles; and control operation of the compression sleeve based at least on the change in estimated volume of the body area.

According to some embodiments, the device is for the use in preventing deep vein thrombosis (DVT). According to some embodiments, the device is for the use in treating lymphedema, peripheral edema and venous stasis edema.

According to some embodiments, the controller is further configured to calculate a reliability score of the estimated change in the volume of the body part.

According to some embodiments, controlling the operation of the compression sleeve comprises changing or releasing the pressure in at least one bladder when the volume of the body part exceeds a predetermined threshold value or when the estimated change indicates an increase of the body part's volume. According to some embodiments, releasing the pressure from the compression sleeve and/or terminating the compression therapy may enable a clinician to evaluate the patient for potential development of a DVT in which case the clinician may decide to discontinue treatment to prevent risk of pulmonary embolism and optionally to prescribe medication to reduce the clot in the leg. According to some embodiments, the device further comprises an alarm configured to be triggered when the volume of the body part exceeds a predetermined threshold value, when the estimated change indicates an increase of the body part's volume and/or when the reliability score crosses a predetermined threshold.

According to some embodiments, an increase in the time required for inflating the at least one bladder from the predetermined vacuum level to the predetermined second pressure level may be indicative of a decrease in the body part's volume, and a decrease in the time required for inflating the at least one bladder from the predetermined vacuum level to the predetermined pressure level may be indicative of an increase in the body part's volume.

According to some embodiments, estimating the change in the treated body part's volume comprises comparing the estimated change to a desired predetermined change and controlling the operation of the compression sleeve based on a deviation of the estimated change from the desired predetermined change. According to some embodiments, comparing the estimated change of the body part's volume to the desired predetermined change further comprises calculating a reliability score based on the deviation of the estimated change from the desired predetermined change.

According to some embodiments, the estimated change in the volume of the subject's body part, such as an increase in the volume of the body part, can be evaluated statistically by comparing to pre-stored treatment data thereby providing an indication and/or prediction of the subject's response to the compression therapy. This data can then be provided to the operator or the treating clinician.

According to some embodiments, the device further comprises a pressure sensor adapted to measure the pressure level in the at least one bladder. According to some embodiments, the pressure sensor may be configured to constantly measure the pressure level in the at least one bladder. Alternatively, the pressure sensor may be configured to measure the pressure level in the at least one bladder at predetermined time intervals. Alternatively, the pressure sensor may be configured to measure the pressure level in the at least one bladder at predetermined time points.

According to some embodiments, the at least one bladder comprise a valve. According to some embodiments, the controller may be further configured to control the operation of the valve. According to some embodiments, the controller may be configured to open the valve when the volume of the treated area exceeds a predetermined threshold value or when the estimated change indicates an increase of the body part's volume.

According to some embodiments, controlling the operation of the compression sleeve comprises controlling the operation of a compressor. According to some embodiments, the compressor may be configured to inflate the at least one bladder. According to some embodiments, the compressor may be configured to inflate the at least one bladder at a constant rate of inflation.

According to some embodiments, controlling the operation of the compression sleeve comprises controlling the operation of a pump. According to some embodiments, the pump may be configured to deflate the at least one bladder. According to some embodiments, the pump may be configured to create a vacuum in the at least one bladder.

According to some embodiments, the at least one bladder is a single bladder. Alternatively, the at least one bladder comprises at least two bladders configured to be sequentially inflated. Alternatively, the at least one bladder comprises at least two bladders configured to be simultaneously inflated.

There is provided, according to some embodiments, a method for providing compression therapy to a subject's body part, the method comprising:

applying a compression sleeve around the subject's body part, the sleeve comprising at least one bladder configured to be inflated and deflated such that an enhanced circulation is achieved;

estimating a change in a volume of the subject's body part by determining a change in the time required for inflating at least one bladder from a predetermined vacuum level to a predetermined pressure level obtained during at least two inflation cycles; and controlling operation of the compression sleeve based at least on the estimated change in the body part's volume.

According to some embodiments, the method is for preventing DVT. According to some embodiments, the method is for treating lymphedema, peripheral edema and venous stasis edema.

According to some embodiments, the method includes estimating a change in the volume of the body part based on at least three inflation cycles.

According to some embodiments, when the volume of the body part exceeds a predetermined threshold value or when the estimated change indicates an increase of the body part's volume, pressure is released from the compression sleeve thereby reducing compression of the body part. According to some embodiments, when the volume of the body part exceeds a predetermined threshold value or when the estimated change indicates an increase of the body part's volume, the pressure in the at least one bladder may be released. According to some embodiments, when the volume of the body part exceeds a predetermined threshold value or when the estimated change indicates an increase of the body part's volume, the pressure in the at least one bladder may be reduced.

According to some embodiments, when the volume of the body part exceeds a predetermined threshold value or when the estimated change indicates an increase of the body part's volume, compression therapy may be paused to enable assessment of the possible formation of a DVT or which would contraindicate continuing therapy. According to some embodiments if formation of DVT identified compression therapy may be is terminated. According to some embodiments, releasing the pressure from the compression sleeve and/or terminating the compression therapy reduces the risk of pulmonary embolism. Alternatively, if formation of DVT or other contraindication is excluded compression therapy may be continued. It is understood, that the continued compression therapy may be done applying a same, an increased or a decreased pressure level. Each possibility is a separate embodiment.

According to some embodiments, an increase in the time required for inflating the at least one bladder from the predetermined vacuum level to the predetermined pressure level indicates a decrease in the body part's volume, and a decrease in the time required for inflating the at least one bladder from the predetermined vacuum level to the predetermined pressure level may be indicative of an increase in the body part's volume.

According to some embodiments, the method further comprises triggering an alarm when the volume of the body part exceeds a predetermined threshold value or when the estimated change indicates an increase of the body part's volume.

According to some embodiments, estimating the change in the body part's volume comprises comparing the estimated change to a desired predetermined change. According to some embodiments, controlling the operation of the compression sleeve includes determining a deviation of the estimated change from the desired predetermined change. According to some embodiments, comparing the estimated change of the body part's volume to the desired predetermined change further includes calculating a reliability value of the deviation of the estimated change from the desired predetermined change.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
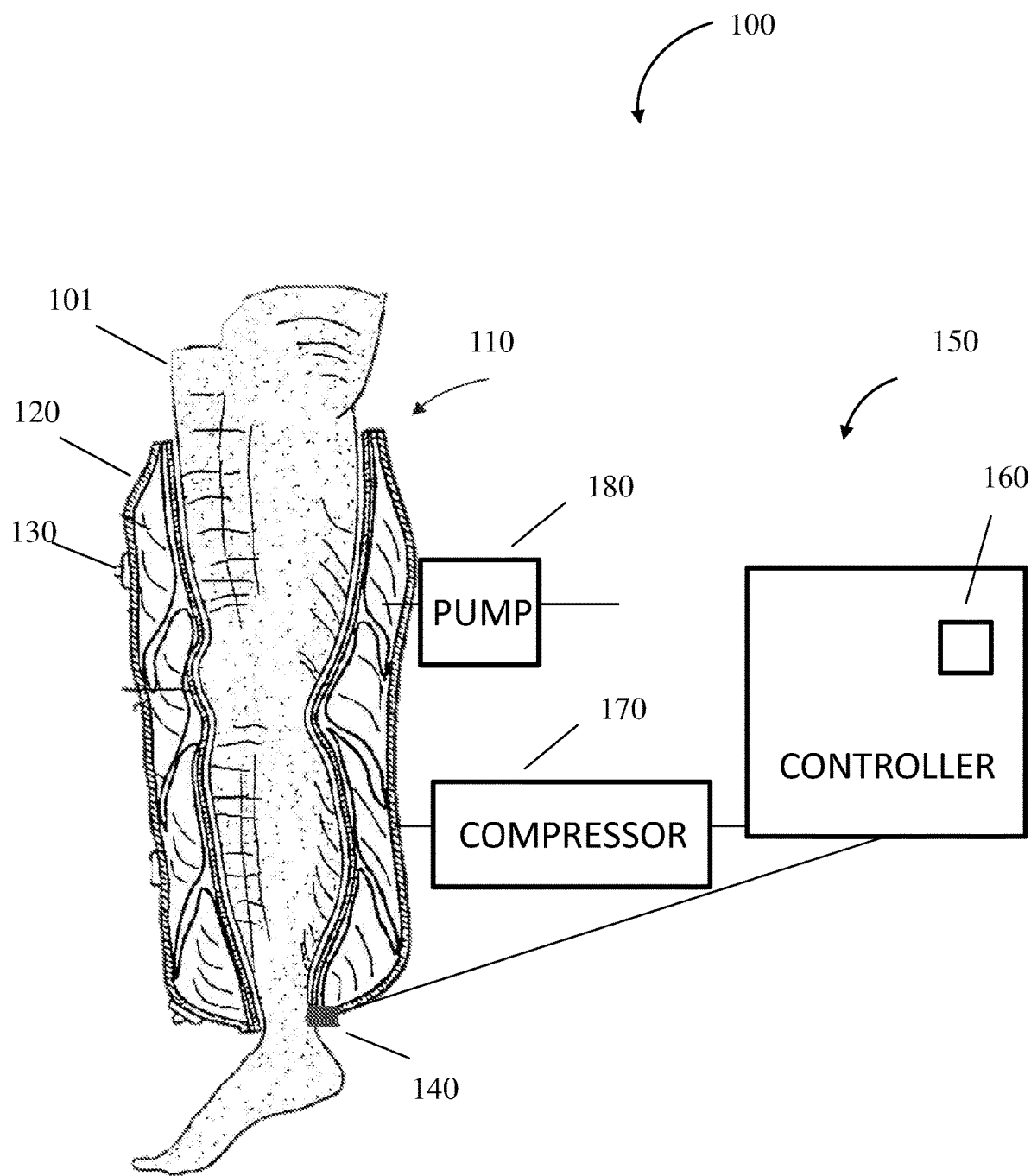
FIG. 1 shows a perspective view of an exemplary device for compression therapy of a subject's body part in accordance with some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates to methods and devices for providing compression therapy (pneumomassage) to a subject in need thereof. According to some embodiments, the disclosure relates to methods and devices for providing compression therapy to a subject's body part by applying a compression sleeve around the subject's body part, the sleeve comprising at least one bladder configured to be inflated and deflated such that enhanced circulation is achieved.

According to some embodiments the methods and devices, disclosed herein, enable estimating the change in a volume of the body part by determining the time required for the pressure level in the bladder to change from a first pressure level to a second predetermined pressure level. According to some embodiments, the method and devices disclosed herein, enable estimating the change in a volume of the body part during and after the compression therapy. According to some embodiments, the method and devices further enable controlling the operation of the compression sleeve based at least on the estimated change in the body part's volume. According to some embodiments the methods and devices, disclosed herein, enable estimating the volume of the body part by determining the time required for inflating the bladder from a predetermined vacuum level to a predetermined pressure level; and controlling operation of the compression sleeve based at least on the estimated volume of the body part.

There is provided, according to some embodiments, method and device for pneumomassage of a subject's body part, comprising: a compression sleeve surroundingly engageable with the body part, the sleeve comprising at least one bladder configured to be inflated and deflated such that enhanced circulation is achieved; a controller configured to calculate and/or estimate a change in a volume of the subject's body part by determining a change in the time required for a pressure level in the at least one bladder to change from a predetermined first pressure level to a predetermined second pressure level during at least two inflation cycles; and control operation of the compression sleeve based at least on the estimated volume of the body part. According to some embodiments, the controller is configured to estimate the volume of the subject's body part by determining a change in the time required for inflating the at least one bladder from a predetermined vacuum level to a predetermined pressure level.

It is understood to the skilled in the art that the compression sleeve may be accommodated to any body part such as, but not limited to a limb (e.g. an arm or a leg), parts of a body area, such as part of a body limb, (e.g. an upper arm, a lower arm, a hand, a lower leg or an upper leg. Each possibility is a separate embodiment. Alternatively, the compression sleeve may be a compression bag configured to be used for the entire body (from torso to toe), or for the entire lower body (from hip to toe) or to the upper torso (chest, back, or shoulders). Each possibility is a separate embodiment. According to some embodiment, the compression sleeve further comprises at least one securing strap configured to firmly secure the sleeve around the subject's body part. Alternatively other means for fastening the sleeve may be used such as zippers, clips', VELCRO™ fasteners or other suitable fasteners. Each possibility is a separate embodiment.

As used herein the terms "compression therapy" and "pneumomassage" may interchangeably refer to removing excess fluid from a treated area to the trunk of the body, typically by means of inflatable pressure sleeves wrapped around the treated area whereby the fluids are absorbed in the circulatory system and excreted from the body.

As used herein the term "volume" with regards to a body part may refer to the volume of part of the body covered by the compression sleeve. According to some embodiments, the volume may refer to the volume of a sub-region of the body part covered by and/or treated with the compression sleeve. For example, the volume may be determined for the lower art, while the entire arm is covered by and/or treated with the compression sleeve.

According to some embodiments, estimating a change in the volume of the body part may be based on the time required for a pressure level to change from a predetermined first pressure level to a predetermined second pressure level during at least two inflation cycles in a plurality of bladders. According to some embodiments, the time required for a pressure level to change from a predetermined first pressure level in the plurality of bladders may be the same. According to some embodiments, the time required for a pressure level to change from a predetermined first pressure level the plurality of bladders may be different. As used herein the term "plurality" with regards to bladders may refer to more than 1, more than 5, more than 10 or more than 15 bladders. Each possibility is a separate embodiment.

According to some embodiments, estimating the time required for a pressure level to change from a predetermined first pressure level to a predetermined second pressure level in the plurality of bladders may enable determining the change in the volume of one or more regions of the treated body part. As a non-limiting example, when providing pneumomassage to a body part (e.g. an arm), the time required for a pressure level to change from a predetermined first pressure level to a predetermined second pressure level in a first of the plurality of bladders may enable to determine a volume of a first region of the body part (e.g. the lower arm), whereas the time required for a pressure level to change from a predetermined first pressure level to a predetermined second pressure level in a second of the plurality of bladders may enable to determine a volume of a second region of the body part (e.g. the upper arm). It is understood that, each region of the body part may be covered/treated with 1, 2, 3 or more of the plurality of bladders and thus the volume of the region may be determined based on the time required for a pressure level to change from a predetermined first pressure level to a predetermined second pressure level in the 1, 2, 3 or more of the plurality of bladders.

According to some embodiments, estimating the time required for a pressure level to change from a predetermined first pressure level to a predetermined second pressure level in the plurality of bladders may enable determining the change in the volume of sections along the treated body part. As a non-limiting example, when providing pneumomassage to a body part (e.g. a leg), the time required for a pressure level to change from a predetermined first pressure level to a predetermined second pressure level in the plurality of bladders may enable to determine a volume of a plurality of sections of the body part separately (e.g. a plurality of sections (for example every 5 cm) of the arm). It is understood that, each section of the body part may be covered/treated with 1, 2, 3 or more of the plurality of bladders and thus the volume of the section may be determined based on the time required for a pressure level to change from a predetermined first pressure level to a predetermined second pressure level in the 1, 2, 3 or more of the plurality of bladders.

According to some embodiments, estimating the volume of the subject's body part comprises estimating the girth of the body part.

As used herein the term "controller" refers to a device configured to execute the operations described herein.

As used herein the terms "inflation cycle" and "inflation/deflation cycle" may be interchangeably used and may refer to one successive inflation and deflation of the at least one bladder.

As used herein, the term "at least two" with regards to inflation cycles may refer to 2, 3, 4, 5, 10 or more inflation cycles. Each possibility is a separate embodiment.

According to some embodiments, the controller is configured to calculate and/or estimate a change in the volume of the body part based on a plurality of inflation cycles. As used herein the term "plurality" with regards to inflation cycles may refer to more than 5, more than 10 or more than 15 inflation cycles. Each possibility is a separate embodiment.

As used herein the term "predetermined vacuum level" may refer to a pressure level obtained in a completely emptied bladder. The predetermined vacuum level may refer to 760 mmHg or below, 500 mmHg or below, 100 mmHg or below, 25 mmHg or below, 1 mmHg or below, 0.1 mmHg or below, 0.01 mmHg or below, 0.001 mmHg or below $1 \times 10^{-9}$ or below, $1 \times 10^{-12}$ or below or any pressure level within the range of 0-760 mmHg. Each possibility is a separate embodiment. Alternatively, the predetermined vacuum level may refer to a vacuum obtained when using a vacuum pump for a predetermined amount of time, such as, but not limited to at least 30 seconds.

According to some embodiments, the device is for the use in preventing DVT. According to some embodiments, the device is for use in treating lymphedema, peripheral edema and venous stasis edema. It is understood by the skilled in the art that the device may also be used for treatment and/or prevention of additional medical conditions such as but not limited tophlebitis, thrombosis, post vein surgery, and to relieve all manifestations of chronic venous disease (heavy legs, varicose veins, leg ulcers). Likewise, the device may also find use in preventing venous troubles during pregnancy and long distance travel.

According to some embodiments, the at least one bladder may be repeatedly inflated and deflated. According to some embodiments, the time required for inflating the at least one bladder from the predetermined vacuum to the predetermined pressure level may be repeatedly determined As used herein the term "repeatedly" may refer to at least twice, at least three times, at least four times, at least five times, at least 10 times, a plurality of times or any other suitable number of times. Each possibility is a separate embodiment.

It is understood that by the skilled in the art that repeatedly measuring the time required for inflating the at least one bladder to change from the predetermined first pressure level to the predetermined second pressure level may enable to derive a trend in the volume of the subject's body part during the pneumomassage treatment. Non-limiting examples of possible trends include, a continuous decrease in the volume, a lack of change in the volume may be observed during the entire treatment, a continuous increase in the volume may be observed, an initial increase in the volume followed by stagnation may be observed, an initial steep decrease followed by a more moderate increase may be observed as well as other possible trends. It is understood to the skilled in the art that statistical methods known in the art may be applied when determining the trend.

According to some embodiments, each trend observed may be assigned a "treatment score" indicative of the treatment efficacy. For example a continuous decrease or an initial decreased maintained during repeated inflation cycles may receive a positive treatment score, whereas a continuous increase or an initial increased maintained during repeated inflation cycles may receive a negative treatment score.

According to some embodiments, the repeated determination of the time required for a pressure level in the at least one bladder to change from a predetermined first pressure level to a predetermined second pressure level and/or the determination of a trend therein may enable to provide an indication of the reliability of the observed change in the volume of the body part. The reliability may according to some embodiments be presented as a reliability score. For example, a single observation of an increase in the volume of the body part may be due to an artifact caused for example by the movement of the subject and will therefore receive a low reliability score. As an opposite example a continuous increase (or decrease) in the body part's volume, or an increase (or decrease) in the volume maintained during repeated inflation cycles may receive a high reliability score. It is understood by the skilled in the art that statistical methods known in the art may be applied when calculating the reliability score.

According to some embodiments, controlling the operation of the compression sleeve comprises changing the pressure in the at least one bladder when the volume of the body part crosses a predetermined threshold value, when the estimated change indicates an increase of the body part's volume and/or when the reliability score crosses a predetermined threshold.

According to some embodiments, changing the pressure in the at least one bladder includes increasing the pressure in the at least one bladder, to enhance treatment efficiency.

According to some embodiments, changing the pressure in the at least one bladder includes, reducing the pressure in the at least one bladder, if a contraindication, such as, but not limited to, DVT is obtained. According to some embodiments, reducing the pressure in the at least one bladder comprises deflating the at least one bladder. According to some embodiments, reducing the pressure in the at least one bladder comprises releasing the pressure from the at least one bladder. According to some embodiments, reducing the pressure in the compression sleeve may prevent pulmonary embolism. According to some embodiments, controlling the operation of the compression sleeve comprises releasing the pressure in the at least one bladder when the volume of the body part crosses a predetermined threshold value, when the estimated change indicates an increase of the body part's volume and/or when the reliability score crosses a predetermined threshold. According to some embodiments, controlling the operation of the compression sleeve comprises terminating the inflation of the at least one bladder when the volume of the body part crosses a predetermined threshold value, when the estimated change indicates an increase of the body part's volume and/or when the reliability score crosses a predetermined threshold. According to some embodiments, controlling the operation of the compression sleeve comprises releasing the pressure from the at least one bladder when the volume of the body part crosses a predetermined threshold value, when the estimated change indicates an increase of the body part's volume and/or when the reliability score crosses a predetermined threshold. According to some embodiments, releasing the pressure from the at least one bladder comprises opening a valve. According to some embodiments, pressure is released and/or compression therapy terminated automatically, when the volume of the body part crosses a predetermined threshold value, when the estimated change indicates an increase of the body part's volume and/or when the reliability score crosses a predetermined threshold. It is understood by the skilled in the art that automatically releasing the pressure and/or terminating compression therapy provides a safety measure and avoids continuing the therapy when potentially harmful. According to some embodiments, terminating the inflation of the at least one bladder is done to enable clinician assessment of the possible formation of a DVT which would contraindicate continuing therapy. According to some embodiments, releasing the pressure from the at least one bladder is intended to enable clinician assessment of the possible formation of a DVT, which would contraindicate continuing therapy.

According to some embodiments, the device may further comprise an alarm configured to be triggered when the volume of the body part crosses a predetermined threshold value or when the estimated change indicates an increase of the body part's volume. According to some embodiments, the alarm may be configured to be triggered when the estimated change indicates an increase or a lack of change in the body part's volume. According to some embodiments, the alarm may be configured to be triggered when the estimated change indicates an increase, a lack of change or an insufficient decrease in the body part's volume. Additionally or alternatively, the alarm may be configured to be triggered when the reliability score crosses a predetermined threshold value. Additionally or alternatively, the alarm may be configured to be triggered when the treatment score crossed a predetermined threshold value.

It is understood by the skilled in the art that the predetermined threshold values described herein may refer to values expected to be obtained during a normal treatment session. Additionally or alternatively, the predetermined thresholds values may refer to textbook values or other values suitable to serve as reference values.

According to some embodiments, the device may be configured to communicate treatment data, such as, but not limited to, the time required for inflating the at least one bladder from the predetermined first pressure level (e.g. vacuum) to the predetermined second pressure level and/or the estimated change in the volume of the body part or any other data, to a remote processing device. According to some embodiments, the device may be configured to wirelessly communicate the treatment data. Non limiting examples of suitable processing devices include computer, a laptop, a mobile phone or any other suitable processing/storage device. Each possibility is a separate embodiment. According to some embodiments, the remote processing device is configured to generate a database based on the communicated data. According to some embodiments, the database is accessible to an access permitted user.

According to some embodiments, the treatment device may be configured to store and/or analyze the treatment data. Alternatively, the device itself may include a processor configured to store and/or analyze the treatment data. The device itself may include a display enabling operator retrieval of data.

According to some embodiments, the term "processing device" may refer to a server, a cloud or any other suitable remote computer storage. According to some embodiments, the processing device may be configured to generate a database based on the communicated data. According to some embodiments, the database may be accessible to an access permitted user, such as but not limited to users of the compression device, clinicians, operators or any other authorized personnel. It is understood to one of ordinary skill in the art that the access permits may differ among access permitted users. For example, the patient and/or user of the compression device may be allowed to gain access to his own treatment data only, whereas clinicians may be able to access data received from a plurality of patient/users. According to some embodiments, the remote processing device may be configured to generate and/or store statistical data generated from a plurality of communicated data sets.

According to some embodiment, the remote processing device (or the processor of the device itself) may be configured to determine the continuation, completion and/or termination of a treatment session based on the provided data. According to some embodiments, the processing device may be configured to provide instructions to the controller based on the received treatment data. According to some embodiments, the processing device may be configured to provide information to the user of the compression sleeve as to the progress of the compression treatment and its results.

According to some embodiments, the processing device (or the processor of the device itself) may be configured to provide an analysis of a plurality of treatment sessions. According to some embodiments, the processing device may be configured to compute a statistically significant change in the volume of the body part based on a plurality of treatment sessions. According to some embodiments, the processing device may be configured to provide a treatment assessment based on a plurality of treatment sessions. According to some embodiments, the processing device may be configured to provide a treatment efficiency score based on a plurality of treatment sessions. According to some embodiments, the processing device may be configured to provide a treatment recommendation based on a plurality of treatment sessions.

It is thus understood, that assessing the change in the volume of the body part by determining the time required to inflate the bladder from a predetermined vacuum to a predetermined pressure level offers a fixed reference point (i.e. the essentially completely emptied bladder) which enables both to determine the change in the volume of the body part, but also to compare different treatment sessions. Advantageously, the comparison may be made both for the same patient at different time points, but also between different patients. In effect, treatment sessions stored by the processing device may serve as a continuously increasing library of pre-stored treatment data which may serve as a reference when assessing treatment efficiency of a current treatment session.

On the contrary, when the bladder is not entirely emptied (for example by the operation of a vacuum pump) residual air will always remain in the bladder. The pressure caused by the residual air depends on the girth of the patient's body part, making comparison between treatment sessions impossible.

As used herein the term "treatment session" may refer to a complete compression therapy from initiation to completion. A treatment session includes at least two inflation cycles, such as but not limited to 2, 3, 4, 5, 10 or more inflation cycles. Each possibility is a separate embodiment.

As used herein the term "plurality", with regards to treatment sessions, may refer to 2, 3, 4, 5 or more treatment sessions. Each possibility is a separate embodiment.

According to some embodiments, when the volume of the body part crosses a predetermined threshold value or when the change in the volume of the subject's body part is indicative of an increase of the body part's volume, the controller is configured to release pressure in the compression sleeve and thereby reduce compression of the body part. Additionally or alternatively, estimating the change in the body part's volume comprises comparing the estimated change to a desired predetermined change. According to some embodiments controlling the operation of the compression sleeve includes determining a deviation of the estimated change from the desired predetermined change. According to some embodiments, comparing the estimated change of the body part's volume to the desired predetermined change further comprises calculating a reliability value of the deviation of the estimated change from the desired predetermined change. It is understood by the skilled in the art, that lack of change in the volume of the body part may also be indicative of a possible formation of DVT which would contraindicate continuing therapy. Hence according to some embodiments, when the change in the volume of the subject's body part is indicative of an increase or lack of change in the volume of the subject's body part, the controller is configured to provide an indication to the user, clinician and/or operator, thereby allowing evaluation of potential development of a DVT in which case the clinician may decide to discontinue treatment to prevent pulmonary embolism and/or initiate treatment of the DVT. According to some embodiments, when the change in the volume of the subject's body part is indicative of an increase, lack of change or a decrease smaller than desired, the controller may be configured to release pressure in the compression sleeve and thereby reduce compression of the body part.

According to some embodiments, the estimated change in the volume of the subject's body part, such as an increase in the volume of the body part, can be further evaluated statistically for example by comparing to pre-stored treatment data thereby providing an indication and/or prediction of the subject's response to the compression therapy. It is understood by the skilled in the art that the pre-stored treatment data can be data accumulated during previous compression therapies of the same or different subjects. Additionally, the pre-stored treatment data can be obtained from textbooks or other suitable media. According to some embodiments, the compression therapy is terminated if the statistical evaluation is indicative of possible formation of DVT which would contraindicate continuing therapy.

According to some embodiments, the time required for the pressure level in the at least one bladder to change from the predetermined first pressure level to the predetermined second pressure level may be indicative of a decrease in the body part's volume, and a decrease in the time required for the pressure level in the at least one bladder to change from the predetermined first pressure level to the predetermined second pressure level may be indicative of an increase in the body part's volume.

As used herein, the predetermined first pressure level may refer to the pressure in at least one deflated bladder. Alternatively or additionally, the predetermined first pressure level may be the pressure obtained in a bladder completely emptied of air. It is understood by the skilled in the art that the pressure of a deflated and/or a vacuumed bladder can be difficult to measure. Hence, according to some embodiments, the controller is configured to calculate and/or estimate a change in a volume of a subject's body part by determining a change in the time required for inflating at least one bladder from vacuum to a predetermined pressure level. According to some embodiments, the bladder may be completely emptied of air. According to some embodiments, the term "completely emptied bladder" may refer to a bladder emptied of air by using a vacuum pump for a predetermined amount of time, such as, but not limited to 30 seconds. According to some embodiments, the term "completely emptied bladder" may refer to a bladder having a predetermined vacuum pressure level. It is understood, that in accordance with this embodiment, the volume of the body part is estimated by determining the time required for the emptied bladder to be sufficiently inflated to reach the (second) predetermined pressure level.

Alternatively, the predetermined first pressure may be any pressure value measured during inflation of the bladder such as but not limited to 800 mmHg, 850 mmHg, 900 mmHg, 950 mmHg, 1000 mmHg, 1050 mmHg, 1200 mmHg, 1500 mmHg, values there between or any other suitable pressure within the range of 800-1500 mmHg or 850-1200 mmHg. Each possibility is a separate embodiment. According to some embodiments, the predetermined first pressure level may be any pressure value measured in the completely emptied bladder prior to inflation such as but not limited to 760 mmHg or below, 500 mmHg or below, 100 mmHg or below, 25 mmHg or below, 1 mmHg or below, 0.1 mmHg or below, 0.01 mmHg or below, 0.001 mmHg or below $1 \times 10^{-9}$ or below, $1 \times 10^{-12}$ or below or any pressure level within the range of 0-760 mmHg or 0.1 mmHg-760 mmHg. Each possibility is a separate embodiment.

According to some embodiments, the predetermined (second) pressure level may be the pressure measured in at least one inflated bladder (e.g. a completely inflated bladder). Alternatively, the predetermined first pressure may be any pressure value measured during inflation of the at least one bladder (i.e. prior to reaching a final desired pressure), such as but not limited to 800 mmHg, 850 mmHg, 900 mmHg, 950 mmHg, 1000 mmHg, 1050 mmHg, 1200 mmHg, values there between or any other suitable pressure within the range of 800-1500 mmHg or 850-1200 mmHg. Each possibility is a separate embodiment.

According to some embodiments, the predetermined second pressure level is higher than the predetermined first pressure level. According to some embodiments the predetermined first pressure level and the predetermined second pressure level are measured during inflation of the at least one bladder. According to some embodiments the predetermined first pressure level is determined prior to inflation of the at least one bladder, whereas the predetermined second pressure level is measured during inflation.

According to some embodiments, the predetermined first pressure level is higher than the predetermined second pressure level. According to some embodiments the predetermined first pressure level and the predetermined second pressure level are measured during deflation of the at least one bladder. According to some embodiments the predetermined first pressure level is determined prior to deflation of the at least one bladder, whereas the predetermined second pressure level is measured during deflation.

According to some embodiments, the device further comprises a pressure sensor adapted to measure the pressure level in the at least one bladder. According to some embodiments, the pressure sensor may be configured to constantly measure the pressure level in the at least one bladder. Alternatively, the pressure sensor may be configured to measure the pressure level in the at least one bladder at predetermined time intervals upon initiation of inflation. Exemplary time intervals include, but are not limited to, every 10 seconds, every 30 seconds, every minute, every 2 minutes, every 5 minutes as well as other suitable time intervals such as time intervals in between those recited. Each possibility is a separate embodiment. Alternatively, the pressure sensor may be configured to measure the pressure level in the at least one bladder at predetermined time points upon initiation of inflation. For example, but not limited to, the pressure sensor may be configured to measure the pressure at time points such as, prior to inflation, 10 sec, 30 sec, 1 min and 2 minutes after initiation of inflation.

According to some embodiments the at least one bladders comprises a valve. According to some embodiments, the valve(s) may be an electrically controlled valve(s). According to some embodiments the valve(s) may be in fluid communication with the pressure source (e.g. the compressor) and the at least one bladder. According to some embodiments, the controller may be configured to control the operation of the valve. For example, the controller may open the valve when the estimated change indicates an increase of the body part's volume. For example, the controller may open the valve when the estimated change indicates an increase or a lack of change in the body part's volume. For example, the controller may open the valve when the estimated change indicates an increase, a lack of change or an insufficient decrease in the body part's volume. Additionally or alternatively, the controller may open the valve when the reliability score crosses a predetermined threshold value. Additionally or alternatively, the controller may open the valve when the treatment score crossed a predetermined threshold value. According to some embodiments, the at least one valve may be configured to open automatically when the estimated change indicates an increase of the body part's volume and/or when an otherwise potentially harmful situation is identified.

According to some embodiments, controlling the operation of the compression sleeve comprises controlling the operation of a compressor. According to some embodiments, the compressor is configured to inflate the at least one bladder. According to some embodiments, the compressor is configured to inflate the at least one bladder at a constant rate of inflation. Alternatively, the compressor is configured to inflate the at least one bladder at incrementally decreasing rate of inflation. Alternatively, the compressor is configured to inflate the at least one bladder at incrementally increasing rate of inflation.

According to some embodiments, controlling the operation of the compression sleeve comprises controlling the operation of a pump. According to some embodiments, the pump may be configured to deflate said at least one bladder. According to some embodiments, the pump may be configured to create a predetermined vacuum level in the at least one bladder According to some embodiments, the pump may be configured to deflate the at least one bladder at a constant rate. Alternatively, the pump may be configured to deflate the at least one bladder at incrementally decreasing rate. Alternatively, the pump may be configured to deflate the at least one bladder at incrementally increasing rate.

According to some embodiments, the at least one bladder is a single bladder. Alternatively, the at least one bladder may comprise at least two bladders configured to be sequentially inflated. According to some embodiments the at least one bladder may comprise at least two bladders configured to be simultaneously inflated.

Reference is now made to FIG. 1, which shows a perspective view of an exemplary device 100 for pneumomassage of a subject's body part such as leg 101, in accordance with some embodiments.

Figure 2:
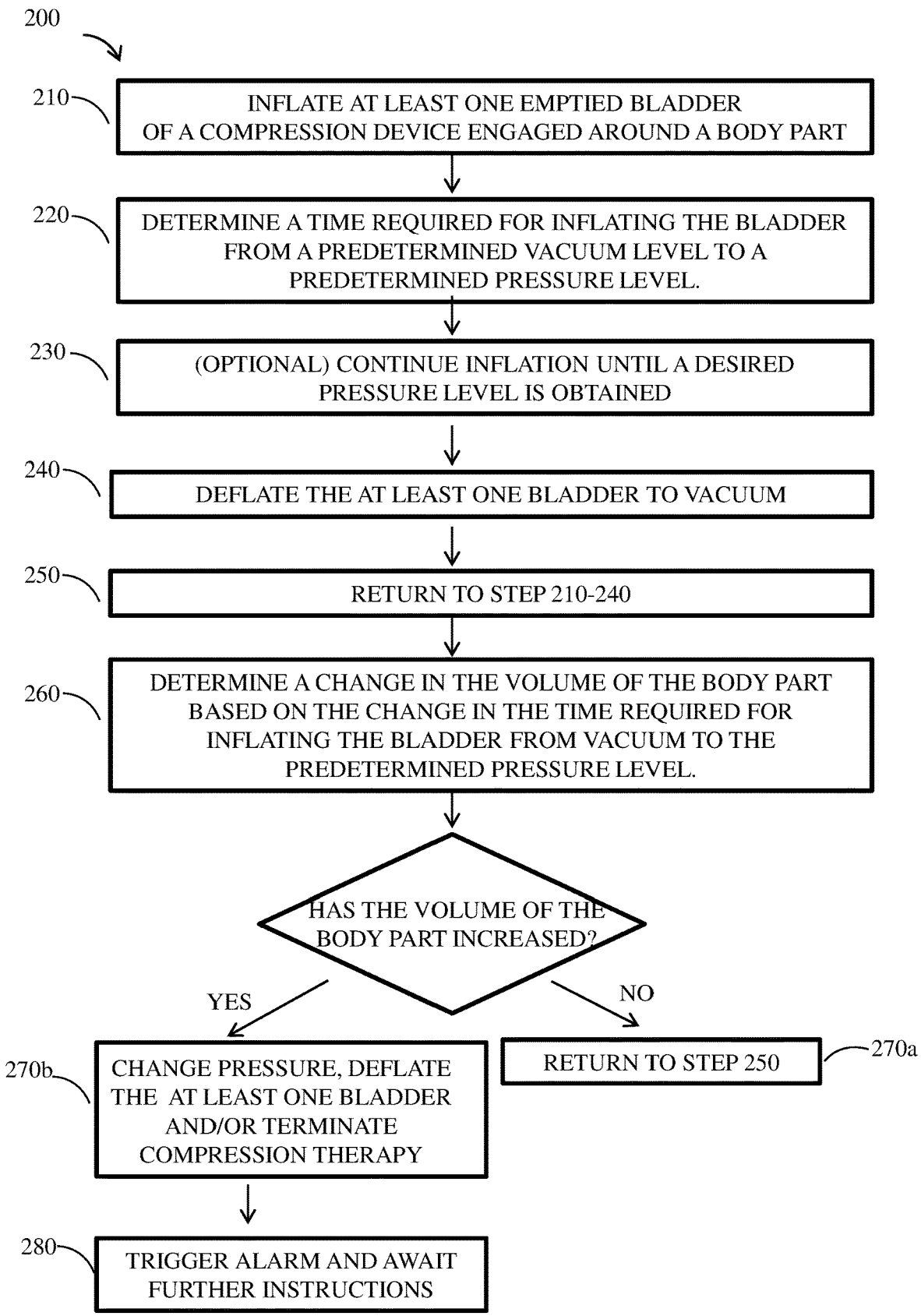
FIG. 2 is an illustrative flowchart depicting the steps of the method in accordance with some embodiments.

In an embodiment, device 100 includes compression sleeve 110 configured to be embrace leg 101. Compression sleeve 110 may be firmly secured around leg 101 by use of securing straps such (not shown). Compression sleeve 110 comprises inflatable bladders such as bladder 120. Compression sleeve 110 may comprises a plurality of bladders as shown in FIG. 2. Alternatively, the sleeve may comprise a single bladder (not shown).

The bladders optionally include a valve, such as valve 130 configured to operate according to signals received from a controller 150. For example, valve 130 may receive a signal to open and release pressure from the inflated bladder, when controller 150 identifies an increase in the volume of leg 101. According to some embodiments, compression sleeve 110 further comprises a pressure sensor such as pressure sensor 140 configured to measure the pressure in bladder 120.

Controller 150 is configured to control the operation of compression sleeve 110, based on an estimate of a change in the volume of leg 101 during treatment. Controller 150 is configured to estimate the change in the volume of leg 101 by determining the time required for inflating bladder 120 from a predetermined vacuum level to a predetermined pressure level. According to some embodiment, the time is calculated according to pressure measurements obtained from pressure sensor 140. Optionally controller 150 may further comprise an alarm 160 configured to be triggered when an inadequate treatment response is observed, such as for example if the volume of leg 101 crosses a predetermined threshold value and/or if the estimated change is indicative of an increase in the volume of leg 101, which may be indicative of formation of DVT.

According to some embodiments, device 100 may further comprise a compressor, such as compressor 170, configured to inflate bladder 120. Operation of compressor 170 may be controlled by controller 150. For example, controller 150 may terminate inflation of bladder 120 by turning off compressor 170 when an inadequate treatment response is observed, such as if the volume of leg 101 crosses a predetermined threshold value and/or if the estimated change is indicative of an increase in the volume of leg 101.

According to some embodiments, device 100 may further comprise a pump, such as pump 180, configured to create a predetermined vacuum level in bladder 120. Operation of pump 180 may be controlled by controller 150. For example controller 150 may initiate deflation of bladder 120 by turning on pump 170 when an inadequate treatment response, such as if the volume of leg 101, crosses a predetermined threshold value and/or if the estimated change is indicative of an increase in the volume of leg 101, which may be indicative of formation of DVT.

Reference is now made to FIG. 2 which is an illustrative flowchart depicting the steps of a method 200 in accordance with some embodiments. In step 210, at least one completely emptied bladder of a compression device surrounding a body part is inflated. In step 220, the time required for inflating the bladder from a predetermined vacuum level to a predetermined pressure level is measured. It is understood by the skilled in the art that the predetermined pressure level may be a pressure level obtained in the completely inflated bladder. Alternatively, the second predetermined pressure level is a pressure level obtained during inflation of the bladder but prior to complete inflation of the bladder. In the latter case inflation is optionally continued in step 230, until the desired pressure level is obtained.

In step 240, the bladder is deflated (to the predetermined vacuum level), for example by turning on a pump. In step 250 the inflation cycle is repeated by returning to steps 210-240. In step 260, the change in the volume of the body part (or part thereof) is determined based on the change in the time required for inflating the bladder from the predetermined vacuum level to the predetermined pressure level. As described hereinabove, this step may further comprise calculating a trend, a treatment score and/or a reliability score according to embodiments of the disclosure. It is understood by the skilled in the art that when the number of inflation/deflation cycles is high, a more reliable trend and/or score may be obtained. It is further understood that the determined change in the subject's body part can be compared to a predetermined desired change in the volume of the subject's body part. Optionally, the estimated change in the volume of the subject's body part, such as an increase in the volume of the body part, can be evaluated statistically by comparing to pre-stored treatment data thereby providing an indication and or prediction of the subject's response to the compression therapy.

According to the estimated change in the volume of the body part, the trend, the treatment score and/or the reliability score the method may continue to additional inflation/deflation cycles, as described in step 270a, by returning to step 250. If the treatment is completed or if an inadequate treatment response is observed, resulting in an increase in the volume of the body part, the method may be interrupted by releasing the pressure and/or deflating the at least one bladder as described in step 270b. It is understood by the skilled in the art that an inadequate treatment response may also be manifested as a lack of change or an insufficient decrease in the volume of the body part. Optionally, in step 280, an alarm may be triggered in order to call for medical attention, such as when the treatment is in hospital settings or in other settings involving professional caregivers. Alternatively, the alarm may be triggered to inform the user that treatment is terminated and professional assistance should be requested, such as when the method is used at home or in other "non-professional" settings.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device for compression therapy of a subject's body part, the device comprising:
   a compression sleeve configured to be surroundingly engageable with the body part, said sleeve comprising at least one bladder configured to be inflated and deflated such that an enhanced circulation is achieved; and
   a controller configured to:
   trigger an essentially complete emptying of the at least one bladder;
   trigger inflation of the at least one bladder to a predetermined pressure level;
   repeatedly determine a change in a time required for inflating the at least one completely emptied bladder to a predetermined pressure level;
   continuously calculate a change in the volume of the body part based on the determined change in time obtained during at least two consecutive inflation cycles;
   calculate a reliability score of the calculated change in the volume of the body part, based on deviation of the calculated change from a desired predetermined change; and
   control operation of said compression sleeve based at least on the calculated change in the volume of the body part and on whether the calculated reliability score crosses a predetermined threshold by reducing the pressure in said at least one bladder and/or terminating the compression therapy when the calculated change in the volume of the body part and the reliability score are indicative of an increase of the body part's volume.

2. The device of claim 1, further configured to communicate the change in the volume of the body part to an operator.

3. The device of claim 1, further comprising an alarm configured to be triggered when the calculated change indicates an increase of the volume of the body part.

4. The device of claim 1, further comprising a pressure sensor adapted to measure the pressure level in the at least one bladder.

5. The device of claim 1, wherein said controller is configured to open a valve when the calculated change in the volume of the body part indicates an increase of the body part's volume.

6. The device of claim 1, wherein controlling the operation of the compression sleeve comprises controlling the operation of a compressor, said compressor configured to inflate said at least one bladder.

7. The device of claim 1, wherein controlling the operation of the compression sleeve comprises controlling the operation of a pump, said pump configured to create a predetermined pressure level in said at least one bladder.

8. The device of claim 1, wherein said at least one bladder comprises at least two bladders configured to be sequentially inflated.

9. The device of claim 1, wherein calculating the change in the body part's volume comprises comparing the calculated change to a desired predetermined change and wherein controlling the operation of the compression sleeve is further based on the deviation of the calculated change from the desired predetermined change.

10. The device of claim 1, further configured to communicate data comprising the time required for inflating the at least one bladder from a predetermined vacuum level to a predetermined pressure level and/or the calculated change in the volume of a body part to a remote processing device.

11. The device of claim 10, wherein said remote processing device is configured to generate a database based on the communicated data, said database being accessible to an access permitted user.

12. A method for providing compression therapy to a subject's body part, the method comprising:
   applying a compression sleeve around the subject's body part;
   providing compression therapy to the body part by repeatedly inflating and deflating the at least one bladder of the sleeve during at least two inflation cycles;
   triggering an essentially complete emptying of the at least one bladder;
   triggering inflation of the at least one bladder to a predetermined pressure level;
   repeatedly determining a change in the time required for inflating the at least one completely emptied bladder to a predetermined pressure level;
   continuously calculating a change in the volume of the body part based on the determined change in time obtained during at least two consecutive inflation cycles;
   calculating a reliability score of the calculated change in the volume of the body part, based on deviation of the calculated change from a desired predetermined change; and
   controlling operation of the compression sleeve based at least on the calculated change in the volume of the body part and the reliability score, by reducing the pressure in said at least one bladder and/or terminating the compression therapy when the calculated change in the volume of the body part indicates an increase of the body part's volume and when the reliability score crosses a predetermined threshold.

13. The method of claim 12, for preventing deep vein thrombosis (DVT) and/or for treating lymphedema, peripheral edema or venous stasis disorders.

14. The method of claim 12, wherein calculating the change in the body part's volume comprises comparing the calculated change to a desired predetermined change, and wherein controlling the operation of the compression sleeve is further based on a deviation of the calculated change from the desired predetermined change.

15. The method of claim 12, further comprising comparing the time required for inflating the at least one bladder from a predetermined vacuum level to a predetermined pressure level and/or the calculated change in the volume of the body part to pre-stored treatment data.

* * * * *